US006323211B1

(12) United States Patent
Garvey et al.

(10) Patent No.: US 6,323,211 B1
(45) Date of Patent: *Nov. 27, 2001

(54) COMPOSITIONS AND METHODS FOR TREATING SEXUAL DYSFUNCTIONS

(75) Inventors: David S. Garvey, Dover; Joseph D. Schroeder, Boston, both of MA (US); Inigo Saenz de Tejada, Madrid (ES)

(73) Assignee: NitroMed, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/285,048

(22) Filed: Apr. 2, 1999

Related U.S. Application Data

(63) Continuation-in-part of application No. PCT/US97/27749, filed on Jan. 28, 1997, and a continuation-in-part of application No. 09/145,143, filed on Sep. 1, 1998, which is a continuation-in-part of application No. 08/714,313, filed on Sep. 18, 1996, now Pat. No. 5,994,294, which is a continuation-in-part of application No. 08/595,732, filed on Feb. 2, 1996, now Pat. No. 5,932,538.

(51) Int. Cl.⁷ .................... A61K 31/44; A61K 31/195
(52) U.S. Cl. .................... 514/280; 514/545; 514/754; 514/929; 514/968; 424/43; 424/400; 424/440; 546/50
(58) Field of Search .................... 514/565, 280, 514/754, 929, 968; 424/43, 400, 460; 546/50

(56) References Cited

U.S. PATENT DOCUMENTS

| | | | |
|---|---|---|---|
| 4,127,118 | 11/1978 | Latorre | 128/79 |
| 4,801,587 | 1/1989 | Voss et al. | 514/248 |
| 4,885,173 | 12/1989 | Stanley et al. | 424/440 |
| 5,059,603 | 10/1991 | Rubin | 514/264 |
| 5,145,852 | 9/1992 | Virag | 514/253 |
| 5,147,655 * | 9/1992 | Ibsen | 424/489 |
| 5,190,967 | 3/1993 | Riley | 514/411 |
| 5,236,904 | 8/1993 | Gerstenberg et al. | 514/12 |
| 5,256,652 | 10/1993 | El-Rashidy | 514/58 |
| 5,380,758 | 1/1995 | Stamler et al. | 514/562 |
| 5,399,581 | 3/1995 | Laragh | 514/396 |
| 5,439,938 | 8/1995 | Snyder et al. | 514/565 |
| 5,447,912 | 9/1995 | Gerstenberg et al. | 514/12 |
| 5,474,535 | 12/1995 | Place et al. | 514/573 |
| 5,492,911 | 2/1996 | Stief | 514/252 |
| 5,543,430 | 8/1996 | Kaesemeyer | 514/562 |
| 5,565,466 | 10/1996 | Gioco et al. | 514/200 |
| 5,567,706 | 10/1996 | Gavras | 519/240 |
| 5,574,068 | 11/1996 | Stamler et al. | 514/562 |
| 5,583,144 | 12/1996 | Kral | 514/321 |
| 5,593,876 | 1/1997 | Stamler et al. | 435/188 |
| 5,607,691 | 3/1997 | Hale et al. | |

(List continued on next page.)

FOREIGN PATENT DOCUMENTS

| | | |
|---|---|---|
| 0346297 | 12/1989 | (EP) . |
| 0357581 | 3/1990 | (EP) . |
| 0432199 | 6/1991 | (EP) . |
| 0611248 | 8/1994 | (EP) . |
| 2547501 | 12/1984 | (FR) . |
| 8-26962 | 1/1996 | (JP) . |
| 8026962 | 1/1996 | (JP) . |
| 9312068 | 6/1993 | (WO) . |
| 9505172 | 2/1995 | (WO) . |
| 9505188 | 2/1995 | (WO) . |
| 9727749 | 8/1997 | (WO) . |
| 9739760 | 10/1997 | (WO) . |
| 9901132 | 1/1999 | (WO) . |
| WO 99/40917 | 4/1999 | (WO) . |

OTHER PUBLICATIONS

Trademark File History for MALE FUEL by Twin Laboratories, Inc., New York, filed Feb. 29, 1996, registered Apr. 29, 1997.

Australian Patent Office, Examiner's First Report, AU Patent Application No. 17562/97 (Feb. 3, 1999).

Goodman and Gilman, *The Pharmacological Basis of Therapeutics*, 8th Ed., p. 229 (1990).

Chen et al, *BJU International*, 83:269–273 (1999).

Mathers et al, *European Urology*, 35(suppl 2):67 (abstract 266) (1999).

RBI/Sigma Catalog, p. 354 (1999).

The Merck Index, 12th Edition, pp. 132, 1727 and 1728 (1996).

Physicians' Desk Reference, 48th Edition, pp. 1146–1147 (1994).

Zorgniotti et al, *Int. J. Impotence Res.*, 6:33–36 (1994).

Trigo–Rocha et al, *Neurourology and Urodynamics*, 13:71–80 (1994).

Miyamoto et al, *Arnzeim.–Forsch./Drug Res.*, 41(II)(12):1216–1221 (1991).

Sonda et al, *Journal of Sex & Marital Therapy*, 16(1):15–21 (1990).

Krane et al, *New England Journal of Medicine*, 321(24):1648–1659 (1989).

Gould et al, *Angiology*, 32(9):595–600 (1981).

Primary Examiner—Bennett Celsa
(74) Attorney, Agent, or Firm—Hale and Dorr LLP

(57) ABSTRACT

The present invention describes methods for preventing and treating sexual dysfunctions in patients by orally administering at least one α-adrenergic receptor antagonist and at least one compound that elevates endogenous nitric oxide or endothelium-derived relaxing factor in vivo. The present invention also describes orally administrable compositions comprising at least one α-adrenergic receptor antagonist and at least one compound that elevates endogenous nitric oxide or endothelium-derived relaxing factor in vivo. In the present invention, the α-adrenergic receptor antagonist is preferably yohimbine or phentolamine, and the compound that elevates endogenous nitric oxide or endothelium-derived relaxing factor in vivo is preferably L-arginine.

67 Claims, No Drawings

U.S. PATENT DOCUMENTS

| | | | |
|---|---|---|---|
| 5,612,314 | 3/1997 | Stamler et al. | 514/13 |
| 5,646,181 | 7/1997 | Fung et al. | 514/506 |
| 5,648,393 | 7/1997 | Stamler et al. | 514/562 |
| 5,698,589 | 12/1997 | Allen | 514/509 |
| 5,731,339 | 3/1998 | Lowrey | 514/400 |
| 5,767,160 | 6/1998 | Kaesemeyer | 514/565 |
| 5,773,457 | 6/1998 | Nahoum | 514/397 |
| 5,789,442 | 8/1998 | Garfield et al. | 514/561 |
| 5,877,216 | 3/1999 | Place et al. | 514/573 |
| 5,910,316 * | 6/1999 | Keefer et al. | 424/433 |
| 5,932,538 | 8/1999 | Garvey et al. | 514/2 |
| 6,165,975 * | 12/2000 | Adams et al. | 514/2 |

* cited by examiner

COMPOSITIONS AND METHODS FOR TREATING SEXUAL DYSFUNCTIONS

RELATED APPLICATIONS

This application is a continuation-in-part of PCT/US97/27749, filed Jan. 28, 1997; and is a continuation-in-part of U.S. application Ser. No. 09/145,143, filed Sep. 1, 1998, which is a continuation-in-part of U.S. application Ser. No. 08/714,313, filed Sep. 18, 1996, issued as U.S. Pat. No. 5,994,294, issued Nov. 30, 1999, which is a continuation-in-part of U.S. application Ser. No. 08/595,732, filed Feb. 2, 1996, issued as U.S. Pat. No. 5,932,538, issued Aug. 3, 1999.

FIELD OF THE INVENTION

The present invention describes methods for treating sexual dysfunctions in patients by orally administering at least one α-adrenergic receptor antagonist and at least one compound that elevates endogenous nitric oxide or endothelium-derived relaxing factor in vivo. The present invention also describes orally administrable compositions comprising at least one α-adrenergic receptor antagonist and at least one compound that elevates endogenous nitric oxide or endothelium-derived relaxing factor in vivo. In the present invention, the α-adrenergic receptor antagonist is preferably yohimbine or phentolamine, and the compound that elevates endogenous nitric oxide or endothelium-derived relaxing factor in vivo is preferably L-arginine.

BACKGROUND OF THE INVENTION

Adequate sexual function is a complex interaction of hormonal events and psychosocial relationships. There are four stages to sexual response as described in the *International Journal of Gynecology & Obstetrics*, 51(3):265–277 (1995). The first stage of sexual response is desire. The second stage of sexual response is arousal. Both physical and emotional stimulation may lead to breast and genital vasodilation and clitoral engorgement (vasocongestion). In the female, dilation and engorgement of the blood vessels in the labia and tissue surrounding the vagina produce the "orgasmic platform," an area at the distal third of the vagina where blood becomes sequestered. Localized perivaginal swelling and vaginal lubrication make up the changes in this stage of sexual response. Subsequently, ballooning of the proximal portion of the vagina and elevation of uterus occurs. In the male, vasodilation of the cavernosal arteries and closure of the venous channels that drain the penis produce an erection. The third stage of sexual response is orgasm, while the fourth stage is resolution. Interruption or absence of any of the stages of the sexual response cycle can result in sexual dysfunction. One study found that 35% of males and 42% of females reported some form of sexual dysfunction. Read et al, *J. Public Health Med.*, 19(4):387–391 (1997).

While there are obvious differences in the sexual response between males and females, one common aspect of the sexual response is the erectile response. As described in U.S. Pat. No. 5,565,466, the disclosure of which is incorporated herein by reference in its entirety, the erectile response in both males and females is the result of engorgement of the erectile tissues of the genitalia with blood which is caused by the relaxation of smooth muscles in the arteries serving the genitalia.

In both pre-menopausal and menopausal females, sexual dysfunction can include, for example, sexual pain disorders, sexual desire disorders, sexual arousal dysfunction, orgasmic dysfunction, dyspareunia, and vaginismus. Sexual dysfunction can be caused, for example, by pregnancy, menopause, cancer, pelvic surgery, chronic medical illness or medications.

In males, some pharmacological methods of treatment are available, however, such methods have not proven to be highly satisfactory or without potentially severe side-effects. Papaverine is now widely used treat impotence. Papaverine is generally effective in cases where the dysfunction is psychogenic or neurogenic and where severe atherosclerosis is not involved. Injection of papaverine, a smooth muscle relaxant, or phenoxybenzamine, a non-specific antagonist and hypotensive, into a corpus cavernosum has been found to cause an erection sufficient for vaginal penetration, however, these treatments are not without the serious and often painful side effect of priapism. Also, in cases where severe atherosclerosis is not a cause of the dysfunction, intracavernosal injection of phentolamine, an α-adrenergic antagonist, is used. As an alternative or, in some cases, as an adjunct to α-adrenergic blockade, prostaglandin $E_1$ ($PGE_1$) has been administered via intracavernosal injection. A major side effect frequently associated with intracorprally delivered $PGE_1$ is penile pain and burning.

There is a need in the art for new and improved treatments of male and female sexual dysfunctions, particularly treatments that do not have the undesirable side effects of those agents currently used. The present invention is directed to these, as well as other, important ends.

SUMMARY OF THE INVENTION

The present invention provides methods for preventing and/or treating sexual dysfunctions and/or enhancing sexual responses in patients, including males and females, by administering to a patient in need thereof a therapeutically effective amount of at least one α-adrenergic receptor antagonist and at least one compound that elevates levels of endogenous nitric oxide or endothelium-derived relaxing factor (EDRF) in vivo. Preferably, the α-adrenergic receptor antagonist is yohimbine or phentolamine. Preferably, the compound that elevates levels of endogenous nitric oxide or EDRF in vivo is L-arginine. In the methods of the present invention, the compounds may be administered separately or as components of the same composition. The compounds and/or compositions are preferably administered from about 1 minute to about 120 minutes prior to sexual activity or intercourse in order to prevent and/or treat sexual dysfunctions and/or to enhance sexual responses in a patient.

In another embodiment, the present invention provides orally administrable compositions comprising a therapeutically effective amount of at least one α-adrenergic receptor antagonist, and at least one compound that elevates levels of endogenous nitric oxide or endothelium-derived relaxing factor (EDRF) in vivo. The invention also provides compositions comprising one or more of such compounds in a pharmaceutically acceptable carrier. The α-adrenergic receptor antagonist is preferably yohimbine or phentolamine. The compound that elevates levels of endogenous nitric oxide or EDRF in vivo is preferably L-arginine.

These and other aspects of the present invention are described in detail herein.

DETAILED DESCRIPTION OF THE INVENTION

The following definitions may be used throughout the specification.

"Patient" refers to animals, preferably mammals, more preferably humans.

"α-adrenergic receptor antagonist" refers to any compound that acts as an antagonist to the α-adrenergic receptor.

"L-arginine" refers to the naturally occurring form of arginine.

"Sexual dysfunction" refers to any sexual dysfunction in a patient, including males and females. Sexual dysfunctions may include, for example, sexual desire disorders, sexual arousal disorders, orgasmic disorders and sexual pain disorders. Female sexual dysfunctions refer to any female sexual dysfunctions including, for example, sexual desire dysfunctions, sexual arousal dysfunctions, orgasmic dysfunctions, sexual pain disorders, dyspareunia, and vaginismus. The female may be pre-menopausal or menopausal. Male sexual dysfunctions refer to any male sexual dysfunctions including, for example, male erectile dysfunction and impotence.

"Pharmaceutically acceptable salts" refer to neutral and acid salts. Pharmaceutically acceptable salts include, for example, those formed with free amino groups, such as those derived from hydrochloric, hydrobromic, hydroiodide, phosphoric, sulfuric, acetic, citric, benzoic, fumaric, glutamic, aspartic, lactic, malic, maleic, succinic, tartaric, p-toluenesulfonic, methanesulfonic acids, gluconic acid, and the like, and those formed with free carboxyl groups, such as those derived from sodium, potassium, ammonium, calcium, ferric hydroxides, isopropylamine, triethylamine, 2-ethylamino ethanol, histidine, procaine and the like.

The present invention is directed to the treatment and/or prevention of sexual dysfunctions in patients, including males and females, by administering the compounds and compositions described herein. The present invention is also directed to enhancing sexual responses in patients, including males and females, by administering the compounds and/or compositions described herein.

Nitric oxide (NO) and NO donors have been recognized as mediators of nonvascular smooth muscle relaxation. As described herein, this effect includes the dilation of the corpus cavernosum smooth muscle, an event involved in the sexual response process for both males and females. However, the effects of NO and NO donor compounds together with α-adrenergic receptor antagonists have not been investigated.

In arriving at the present invention, it was unexpectedly discovered that the risk of toxicities and adverse effects that are associated with high doses of α-adrenergic receptor antagonists can be avoided by the use of such α-adrenergic receptor antagonists in conjunction with one or more compounds that elevate endogenous levels of nitric oxide or endothelium-derived relaxing factor (EDRF). Such toxicities and adverse effects include postural hypotension, reflex tachycardia and other arrhythmias, syncope and, with respect to the ergot alkaloids, nausea and vomiting and, upon prolonged or excessive administration, vascular insufficiency and gangrene of the extremities. The α-adrenergic receptor antagonists and compounds that elevate endogenous levels of nitric oxide or EDRF work together to permit the same efficacy with lower doses of the α-adrenergic receptor antagonists or work synergistically to produce an effect that is greater than the additive effects of the α-adrenergic receptor antagonists and the compounds that elevate endogenous levels of nitric oxide or EDRF.

The α-adrenergic receptor antagonist for use in the present invention can be any known in the art. Preferably, the α-adrenergic receptor antagonist is an imidazoline or an alkaloid.

Imidazolines include phentolamine and tolazoline. Phentolamine is a non-specific $\alpha_1$ and $\alpha_2$ adrenergic receptor antagonist. Phentolamine is used in short-term control of hypertension in patients with pheochromocytoma and direct, intracavernous injection of phentolamine (usually in combination with papaverine and $PGE_1$) has been proposed as a treatment for male sexual dysfunction. Tolazoline is used in the treatment of persistent pulmonary hypertension in neonates. Other imidazolines include, for example, idazoxan, deriglidole, RX 821002, BRL 44408 and BRL 44409 (see, Young et al, *Eur. J. Pharm.*, 168:381–386 (1989), the disclosure of which is incorporated herein by reference). Preferably, the imidazoline is phentolamine. Phentolamine may be provided in a free-base form or in the form of a pharmaceutically acceptable salt. Phentolamine is preferably in the form of phentolamine hydrochloride or phentolamine mesylate, more preferably phentolamine mesylate.

Alkaloids include, for example, yohimbine, apoyohimbine, β-yohimbine, yohimbol, pseudoyohimbine and epi-3α-yohimbine. These compounds are competitive antagonists that are selective for $\alpha_2$-adrenergic receptors. In humans, these compounds have been observed to increase blood pressure and heart rate and has been used in the treatment of male sexual dysfunction. Preferably the α-adrenergic receptor antagonist is yohimbine, which is the principle alkaloid of the bark of the Corynanthe yohimbine tree. Yohimbine can be provided in the form of a plant extract containing yohimbine, preferably, yohimbe bark powder or yohimbe bark extract. Yohimbine may also be provided in a free-base form or in the form of a pharmaceutically acceptable salt. Yohimbine is preferably in the form of yohimbine hydrochloride, yohimbe bark powder or yohimbe bark extract, more preferably yohimbine hydrochloride. Yohimbine hydrochloride is commercially available, for example, under the trade name Yocon® (Glenwood Laboratories, Tenafly, N.J.) and Yohimbine Houde (Laboratories Hoechst Houde, France).

Each of the above contemplated α-antagonists is described more fully in the literature, such as in Goodman and Gilman, The Pharmacological Basis of Therapeutics (9th Edition), McGraw-Hill (1996), the disclosure of which is incorporated by reference herein in its entirety.

The compounds of the present invention that stimulate endogenous synthesis of nitric oxide or elevate levels of endogenous nitric oxide or endothelium-derived relaxing factor (EDRF) in vivo can be any such compounds known in the art. Such compounds include, for example, L-arginine and N-hydroxy-L-arginine, including their nitrosated and nitrosylated analogs (e.g., nitrosated L-arginine, nitrosylated L-arginine, nitrosated N-hydroxy-L-arginine, nitrosylated N-hydroxy-L-arginine), precursors of L-arginine and N-hydroxy-L-arginine and/or physiologically acceptable salts thereof, including for example, citrulline, ornithine or glutamine, and the substrates for nitric oxide synthase, cytokines, adenosine, bradykinin, calreticulin, bisacodyl, phenolphthalein, and endothelium. EDRF is a vascular relaxing factor secreted by the endothelium, and has been identified as nitric oxide (NO) or a closely related derivative thereof. (Palmer et al, *Nature*, 327:524–526 (1987), Ignarro et al, *Proc. Natl. Acad. Sci. USA,* 84:9265–9269 (1987)).

In the present invention, the preferred compound that stimulates endogenous synthesis of nitric oxide or elevates levels of endogenous nitric oxide or EDRF is L-arginine. L-arginine is an over-the-counter food supplement, and can be used in free-base form or in the form of a pharmaceutically acceptable salt. L-arginine is preferably in the form of L-arginine hydrochloride or L-arginine glutamate, more preferably L-arginine glutamate. L-arginine glutamate is commercially available from, for example, Teknova, Half Moon Bay, Calif.; Triple Crown America, Inc., Perkasie, Pa.; Kelatron Laboratories, Ogden, Utah; Advanced Chem Tech, Inc., Louisville, Ky.; Novartis Pharma SA, France (under the name Dynamisan®).

In another aspect, the present invention provides methods of treating and/or preventing sexual dysfunctions and/or enhancing sexual responses in a patient in need thereof by administering to the patient a therapeutically effective amount of at least one α-adrenergic receptor antagonist, and at least one compound that elevates levels of endogenous nitric oxide or EDRF in vivo. The compounds can be administered separately or as components of the same composition. The α-antagonist can be any α-antagonist described herein, preferably yohimbine or phentolamine. The compound that elevates endogenous nitric oxide or EDRF can be any such compound described herein, preferably L-arginine.

The dosage regimen for preventing and/or treating sexual dysfunctions and/or enhancing sexual responses with the compounds and/or compositions of the present invention is selected in accordance with a variety of factors, including the type, age, weight, sex, diet and medical condition of the patient, the severity of the sexual dysfunction, the route of administration, pharmacological considerations such as the activity, efficacy, pharmacokinetic and toxicology profiles of the particular compound used, whether a drug delivery system is used and whether the compound is administered as part of a drug combination. Thus, the dosage regimen actually used may vary widely and therefore may deviate from the preferred dosage regimen set forth herein. Dosage unit compositions may contain such amounts or submultiples thereof to make up the daily dose.

In one embodiment of the present invention, the α-antagonist, such as yohimbine, is administered in an amount of about 1.0 mg to about 18.0 mg (equivalent to about 1.1 mg to about 19.8 mg yohimbine hydrochloride), preferably about 4.5 mg to about 6.4 mg, (equivalent to about 5.0 mg to about 7.0 mg yohimbine hydrochloride), more preferably about 5.0 mg to about 6.0 mg, (equivalent to about 5.5 mg to about 6.5 mg yohimbine hydrochloride), most preferably about 5.5 mg (equivalent to about 6.0 mg yohimbine hydrochloride ). The yohimbine can also be administered in the form of yohimbe bark powder or extract that has been standardized to deliver up to about 18 mg of yohimbine. In conjunction therewith, L-arginine is administered in an amount of about 0.25 grams to about 10 grams (equivalent to about 0.5 grams to about 20 grams of L-arginine glutamate), preferably about 2 grams to about 4 grams (equivalent to about 4 grams to about 8 grams of L-arginine glutamate); more preferably about 2.5 grams to about 3.5 grams (equivalent to about 5 grams to about 7 grams of L-arginine glutamate); most preferably about 3 grams (equivalent to 6 grams of L-arginine glutamate).

In another embodiment of the present invention, the α-antagonist, such as phentolamine, is administered in an amount of about 3.7 mg to about 90 mg (equivalent to about 5 mg to about 120 mg phentolamine mesylate), preferably about 22 mg to about 37 mg (equivalent to about 30 mg to about 50 mg phentolamine mesylate), more preferably about 26 mg to about 34 mg (equivalent to about 35 mg to about 45 mg phentolamine mesylate), even more preferably about 28 mg to about 31 mg (equivalent to about 38 mg to about 42 mg phentolamine mesylate), most preferably about 30 mg (equivalent to about 40 mg phentolamine mesylate). In conjunction therewith, L-arginine is administered in an amount of about 0.25 grams to about 10 grams (equivalent to about 0.5 grams to about 20 grams of L-arginine glutamate), preferably about 2 grams to about 4 grams (equivalent to about 4 grams to about 8 grams of L-arginine glutamate); more preferably about 2.5 grams to about 3.5 grams (equivalent to about 5 grams to about 7 grams of L-arginine glutamate); most preferably about 3 grams (equivalent to 6 grams of L-arginine glutamate).

The compounds of the present invention can be administered orally, bucally, parenterally, topically or rectally in dosage unit formulations containing conventional nontoxic pharmaceutically acceptable carriers, adjuvants, and vehicles, as desired. Preferably, the compounds and/or compositions are administered orally.

Solid dosage forms for oral administration can include capsules, tablets, chewable tablets, wafers, pills, effervescent tablets, powders (including effervescent powders), granules, gels, lozenges, troches, and encapsulated powders. In such solid dosage forms, the active compound(s) may be admixed with at least one inert diluent or carrier, such as sucrose lactose or starch. Such dosage forms may also comprise, as in normal practice, additional substances other than inert diluents, e.g., lubricating agents such as magnesium stearate. In the case of capsules, tablets, chewable tablets, effervescent tablets, powders (including effervescent powders), and pills, the dosage forms may also comprise buffering agents. Tablets and pills can also be prepared with enteric coatings. Solid dosage forms can also comprise sweetening and flavoring agents. Powders (including effervescent powders) can also comprise anti-caking agents, such as cellulose.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compositions of the present invention can also include other components, including, for example, vitamins (such as, for example, Vitamin A, Vitamin C, Vitamin E, Vitamin B-5, thiamin, riboflavin, and the like); minerals (such as, for example, zinc, selenium, and the like); plant extracts (such as, for example, Ginkgo, Ginseng, Saw Palmetto berry, St. John's Wort, Avena Sativa, and the like); antioxidants (such as, for example, ascorbic acid, and the like); hormones (such as, for example, dehydroepiandrosterone, and the like); and amino acids (such as, for example, L-tyrosine, and the like).

In one embodiment of the present invention, the α-antagonist (such as yohimbine or phentolamine) and L-arginine are administered as separate components. Preferably, the α-antagonist (such as yohimbine or phentolamine) is administered in the form of an oral tablet or an oral wafer; and L-arginine is prepared either in the form of an oral tablet (including effervescent tablet) or powder (including effervescent powder) that is dissolved in a liquid before being orally ingested. When the α-antagonist and L-arginine are administered as separate components in the methods of the present invention, they are preferably administered to the patient at about the same time. "About the same time" means that within about thirty minutes of administering one compound (e.g., the α-antagonist or L-arginine) to the patient, the other compound (e.g., L-arginine or the α-antagonist) is administered to the patient. "About the same time" also includes simultaneous administration of the compounds.

In another embodiment of the present invention, the α-antagonist (such as yohimbine or phentolamine) and L-arginine are components in the same composition. The composition may be in the form of a powder (including effervescent powder) or tablet (including effervescent tablet), wherein the powder or tablet can be dissolved in a liquid before being orally ingested. In either case, the powder (including effervescent powder) or tablet (including effervescent tablet) are capable of dissolving in a liquid to form a solution or suspension. The powder (including effervescent powder) or tablet (including effervescent tablet) can be vigorously stirred in the liquid to facilitate dissolution. The liquid can be any known in the art, such as water, milk, flavored drink, juice, and the like.

While the compounds and/or compositions of the present invention may be administered on a regular basis, they are preferably administered as a single dose prior to sexual activity or intercourse. Such single dose administration prior to sexual activity or intercourse allows for the prevention and/or treatment of a sexual dysfunction in a patient and/or enhances sexual responses in a patient.

For example, in the methods of the present invention, the compound(s) and/or composition(s) are generally administered about 15 minutes to about 125 minutes to sexual activity or intercourse; preferably about 30 minutes to about 90 minutes prior to sexual activity or intercourse; more preferably about 45 minutes to about 75 minutes prior to sexual activity or intercourse; even more preferably about 50 minutes to about 70 minutes prior to sexual activity or intercourse; still more preferably about 55 minutes to about 65 minutes prior to sexual activity or intercourse; most preferably about 60 minutes prior to sexual activity or intercourse.

While the compounds and/or compositions of the present invention can be administered as the sole active pharmaceutical agent, they can also be used in combination with one or more other compounds that are known to be effective against sexual dysfunctions, including, for example, vasoactive agents, phosphodiesterase inhibitors, α-adrenergic receptor antagonists, prostaglandins, dopamine agonists, potassium channel openers, endothelin antagonist, and the like.

The present invention also provides a pharmaceutical pack or kit comprising one or more containers filled with one or more of the ingredients of the pharmaceutical compounds of the present invention. Associated with such kit(s) or container(s) can be a notice in the form prescribed by a governmental agency regulating the manufacture, use or sale of pharmaceuticals or biological products, which notice reflects approval by the agency of manufacture, use or sale for human administration.

In a preferred embodiment, the compounds and/or compositions of the present invention are packaged for distribution in a sachet. The sachet can be made of ant material known in the art including, for example, plastic, MYLAR® (polyester films) (Dupont), foil, paper, and the like. The sachet is preferably made of a moisture-resistant material. The compounds and/or compositions of the present invention are removed from the sachet prior to being to being administered to the patient. For ease of use and administration by the patient, each sachet preferably contains a single dose of the compounds and/or compositions of the present invention.

EXAMPLE

The following non-limiting example further describes and enables one of ordinary skill in the art to make and use the invention. The example is for purposes of illustration only and is not intended to limit the scope of the invention or claims.

Example 1

Administration of Yohimbine Hydrochloride and L-arginine Glutamate for the Treatment of Male Sexual Dysfunction A comparative Phase II double blind with double placebo, randomized and controlled single-center study was conducted to determine the efficacy of yohimbine hydrochloride and L-arginine glutamate for the treatment of male sexual dysfunction. Forty eight patients suffering from erectile dysfunction for at least 3 months were identified by a hospital's urology department. The initial evaluation of each patient included a physical examination and a questionnaire-derived sexual history. The questionnaire was self-administered, and the validated International Index of Erectile Function (IIEF) was used to measure the attributes. The median age of the patients was 57 years and none of the patients had any known sensitivity to either yohimbine or L-arginine. The patients were divided into 6 groups of 8 patients each. The overall composition of each group was as closely matched as possible.

There were 3 treatment periods, each lasting 14 days, for a total of 42 days of treatment. The 3 treatment periods were (i) yohimbine hydrochloride and L-arginine glutamate, (ii) yohimbine hydrochloride and L-arginine placebo, and (iii) yohimbine placebo and L-arginine placebo. The yohimbine hydrochloride was administered as a single dose of 6 mg yohimbine hydrochloride. The L-arginine glutamate was administered as a single dose of 6 g arginine glutamate in a drink. The L-arginine and yohimbine placebos were packaged in the same form as the pharmacologically active components. Each patient group was given the 3 treatment regimes in a random order. The patients were instructed to take no more than one treatment per day, on demand, 1–2 hours before sexual intercourse. The patients kept a detailed diary and were required to complete the IIEF questionnaire at the end of each treatment period. The patients took the entire fourteen day period into consideration when giving the average rating to the 15 questions.

Of the forty-eight patients enrolled, three patients withdrew from the study prematurely. The results of the remaining forty-five patients were analyzed statistically The difference in the improvement of sexual dysfunction between the combination of yohimbine and L-arginine relative to placebo was significant (p=0.004), while the difference between yohimbine and placebo was not significant (p=0.223). For global satisfaction, the combination of yohimbine and L-arginine was significantly better than placebo (p=0.022), while the difference between yohimbine and placebo was not significant (p=0.746).

Various modifications of the invention, in addition to those described herein, will be apparent to one skilled in the art from the foregoing description. Such modifications are intended to fall within the scope of the appended claims.

What is claimed is:

1. A method for treating a sexual dysfunction in a patient in need thereof comprising orally administering L-arginine in an amount of about 0.25 grams to about 10 grams or a pharmaceutically acceptable salt thereof and yohimbine in an amount of about 1.0 mg to about 18.0 mg or a pharmaceutically acceptable salt thereof to the patient about 15 minutes to about 125 minutes prior to sexual activity or sexual intercourse to treat the sexual dysfunction.

2. The method of claim 1, wherein the L-arginine is orally administered in an amount of about 3 grams.

3. The method of claim 1, wherein the L-arginine or the pharmaceutically acceptable salt thereof is L-arginine hydrochloride.

4. The method of claim 1, wherein the L-arginine or the pharmaceutically acceptable salt thereof is L-arginine glutamate.

5. The method of claim 4, wherein the L-arginine glutamate is orally administered in an amount of about 6 grams.

6. The method of claim 1, wherein the L-arginine or the pharmaceutically acceptable salt thereof is orally administered in the form of a solid dose.

7. The method of claim 6, wherein the solid dose is in the form of a tablet.

8. The method of claim 6, wherein the solid dose is in the form of a powder.

9. The method of claim 1, wherein the L-arginine or the pharmaceutically acceptable salt thereof is orally administered in the form of a solution or a suspension.

10. The method of claim 1, wherein the yohimbine or the pharmaceutically acceptable salt thereof is yohimbine hydrochloride.

11. The method of claim 1, wherein the yohimbine or the pharmaceutically acceptable salt thereof is yohimbine tartarate.

12. The method of claim 10, wherein the yohimbine hydrochloride is orally administered in an amount of about 6 milligrams.

13. The method of claim 1, wherein the yohimbine or the pharmaceutically acceptable salt thereof is obtained from yohimbe bark powder, yohimbe bark extract or Rauwolfia root.

14. The method of claim 1, wherein the yohimbine or the pharmaceutically acceptable salt thereof is orally administered in the form of a solid dose.

15. The method of claim 14, wherein the solid dose is in the form of a tablet.

16. The method of claim 14, wherein the solid dose is in the form of a powder.

17. The method of claim 1, wherein the yohimbine or the pharmaceutically acceptable salt thereof is orally administered in the form of a solution or suspension.

18. The method of claim 1, wherein the yohimbine or the pharmaceutically acceptable salt thereof and the L-arginine or the pharmaceutically acceptable salt thereof are administered about 30 minutes to about 90 minutes prior to sexual activity or sexual intercourse.

19. The method of claim 18, wherein the yohimbine or the pharmaceutically acceptable salt thereof and the L-arginine or the pharmaceutically acceptable salt thereof are administered about 60 minutes prior to sexual activity or sexual intercourse.

20. The method of claim 1, wherein the yohimbine or the pharmaceutically acceptable salt thereof and L-arginine or the pharmaceutically acceptable salt thereof are in the form of a composition.

21. The method of claim 1, wherein the patient is male.

22. The method of claim 1, wherein the patient is female.

23. The method of claim 1, further comprising removing the L-arginine or the pharmaceutically acceptable salt thereof and the yohimbine or the pharmaceutically acceptable salt thereof from a sachet prior to orally administering the L-arginine or the pharmaceutically acceptable salt thereof and the yohimbine or the pharmaceutically acceptable salt thereof to the patient.

24. The method of claim 1, wherein the L-arginine is in the form of a pharmaceutically acceptable salt.

25. The method of claim 1, wherein the yohimbine is in the form of a pharmaceutically acceptable salt.

26. The method of claim 7, wherein the tablet is an effervescent tablet.

27. The method of claim 8, wherein the powder is an effervescent powder.

28. The method of claim 15, wherein the tablet is an effervescent tablet.

29. The method of claim 16, wherein the powder is an effervescent powder.

30. The method of claim 1, further comprising administering at least one vasoactive agent.

31. The method of claim 30, wherein the at least one vasoactive agent is selected from phosphodiesterase inhibitors, alpha-adrenergic receptor antagonists, prostaglandins, dopamine agonists, potassium channel openers and endothelin antagonists.

32. An orally administrable effervescent composition comprising L-arginine in an amount of about 0.25 grams to about 10 grams or a pharmaceutically acceptable salt thereof and yohimbine in an amount of about 1.0 milligrams to about 18.0 milligrams or a pharmaceutically acceptable salt thereof.

33. The orally administrable effervescent composition of claim 32, wherein the L-arginine is present in an amount of about 3 grams.

34. The orally administrable effervescent composition of claim 32, wherein the L-arginine or the pharmaceutically acceptable salt thereof is L-arginine hydrochloride.

35. The orally administrable effervescent composition of claim 32, wherein the L-arginine or the pharmaceutically acceptable salt thereof is L-arginine glutamate.

36. The orally administrable effervescent composition of claim 35, wherein the L-arginine glutamate is present in an amount of about 6 grams.

37. The orally administrable effervescent composition of claim 32, wherein the yohimbine or the pharmaceutically acceptable salt thereof is yohimbine hydrochloride.

38. The orally administrable effervescent composition of claim 32, wherein the yohimbine or the pharmaceutically acceptable salt thereof is yohimbine tartarate.

39. The orally administrable effervescent composition of claim 32, wherein the yohimbine or the pharmaceutically acceptable salt thereof is obtained from yohimbe bark powder, yohimbe bark extract or Rauwolfia root.

40. The orally administrable effervescent composition of claim 37, wherein the yohimbine hydrochloride is present in an amount of about 6 milligrams.

41. The orally administrable effervescent composition of claim 32, wherein the orally administrable effervescent composition is in an effervescent solid dose form.

42. The orally administrable effervescent composition of claim 41, wherein the effervescent solid dose form is an effervescent tablet.

43. The orally administrable effervescent composition of claim 41, wherein the effervescent solid dose form is an effervescent powder.

44. The orally administrable effervescent composition of claim 41, wherein the effervescent solid dose form is in a sachet.

45. The orally administrable composition of claim 32, wherein the orally administrable effervescent composition is an effervescent solution or an effervescent suspension.

46. The orally administrable effervescent composition of claim 32, further comprising at least one vasoactive agent.

47. The orally administrable effervescent composition of claim 46, wherein the at least one vasoactive agent is selected from phosphodiesterase inhibitors, alpha-adrenergic receptor antagonists, prostaglandins, dopamine agonists, potassium channel openers and endothelin antagonists.

48. A sachet comprising L-arginine in an amount of about 0.25 grams to about 10.0 grams or a pharmaceutically acceptable salt thereof and yohimbine in an amount of about 1.0 milligrams to about 18.0 milligrams or a pharmaceutically acceptable salt thereof, wherein the L-arginine or the pharmaceutically acceptable salt thereof and the yohimbine or the pharmaceutically acceptable salt thereof are in an orally administrable form.

49. The sachet of claim 48, wherein the L-arginine is present in an amount of about 3 grams.

50. The sachet of claim 48, wherein the L-arginine or the pharmaceutically acceptable salt thereof is L-arginine hydrochloride.

51. The sachet of claim 48, wherein the L-arginine or the pharmaceutically acceptable salt thereof is L-arginine glutamate.

52. The sachet of claim 51, wherein the L-arginine glutamate is present in an amount of about 6 grams.

53. The sachet of claim 48, wherein the yohimbine or the pharmaceutically acceptable salt thereof is yohimbine hydrochloride.

54. The sachet of claim 48, wherein the yohimbine or the pharmaceutically acceptable salt thereof is yohimbine tartarate.

55. The sachet of claim 48, wherein the yohimbine or the pharmaceutically acceptable salt thereof is obtained from yohimbe bark powder, yohimbe bark extract or Rauwolfia root.

56. The sachet of claim 53, wherein the yohimbine hydrochloride is present in an amount of about 6 milligrams.

57. The sachet of claim 48, wherein the L-arginine or the pharmaceutically acceptable salt thereof and the yohimbine or the pharmaceutically acceptable salt thereof are in a solid dose form.

58. The sachet of claim 57, wherein the solid dose form is a tablet.

59. The sachet of claim 58, where the tablet is an effervescent tablet.

60. The sachet of claim 57, wherein the solid dose form is a powder.

61. The sachet of claim 60, wherein the powder is an effervescent powder.

62. The sachet of claim 48, wherein the L-arginine or the pharmaceutically acceptable salt thereof and the yohimbine or the pharmaceutically acceptable salt thereof are a solution or a suspension.

63. The sachet of claim 48, wherein the sachet is a moisture-resistant material.

64. The sachet of claim 48, wherein the sachet is plastic, a polyester film, foil or paper.

65. The sachet of claim 48, wherein the sachet comprises a single dose of the L-arginine or the pharmaceutically acceptable salt thereof and the yohimbine or the pharmaceutically acceptable salt thereof.

66. The sachet of claim 48, further comprising at least one vasoactive agent.

67. The sachet of claim 66, wherein the at least one vasoactive agent is selected from phosphodiesterase inhibitors, alpha-adrenergic receptor antagonists, prostaglandins, dopamine agonists, potassium channel openers and endothelin antagonists.

* * * * *